(12) United States Patent
Mahoney

(10) Patent No.: US 8,999,723 B2
(45) Date of Patent: Apr. 7, 2015

(54) TRANSFORMER HYDROGEN INDICATOR

(71) Applicant: Serveron Corporation, Beaverton, OR (US)

(72) Inventor: Steven Mahoney, Beaverton, OR (US)

(73) Assignee: Serveron Corporation, Beaverton, OR (US)

( * ) Notice: Subject to any disclaimer, the term of this patent is extended or adjusted under 35 U.S.C. 154(b) by 0 days.

(21) Appl. No.: 14/254,154

(22) Filed: Apr. 16, 2014

(65) Prior Publication Data

US 2014/0329328 A1 Nov. 6, 2014

Related U.S. Application Data

(60) Provisional application No. 61/818,960, filed on May 3, 2013.

(51) Int. Cl.
*G01N 33/28* (2006.01)
*G01N 21/77* (2006.01)
*G01N 1/22* (2006.01)

(52) U.S. Cl.
CPC .................................. *G01N 33/2841* (2013.01)

(58) Field of Classification Search
USPC ........... 436/60, 144, 164, 165, 167, 169, 181; 422/400, 420, 83, 86, 87, 88, 416; 73/19.1
See application file for complete search history.

(56) References Cited

U.S. PATENT DOCUMENTS

| 4,112,737 A * | 9/1978 | Morgan | 73/19.02 |
| 5,659,126 A * | 8/1997 | Farber | 73/19.02 |
| 6,895,805 B2 * | 5/2005 | Hoagland | 73/31.06 |
| 8,075,675 B2 * | 12/2011 | Mahoney et al. | 96/6 |
| 2008/0206874 A1 * | 8/2008 | Manka | 436/2 |
| 2013/0247647 A1 * | 9/2013 | Mahoney et al. | 73/19.11 |

* cited by examiner

*Primary Examiner* — Maureen Wallenhorst
(74) *Attorney, Agent, or Firm* — Hancock Hughey LLP

(57) ABSTRACT

A reliable, low cost device for determining when dangerous levels of hydrogen gas have been generated in a transformer is disclosed. The hydrogen indicator is defined by a module assembly that threads into either the headspace or into the oil-filled body of a transformer. The module has an open interior that contains a film that incorporates a hydrogen-sensitive chemochromic indicator. The indicator film is visible through a lens. When the film has been exposed to hydrogen, chemical changes in the chemochromic indicator cause the film to change color—the color change is immediately visible through the lens.

19 Claims, 2 Drawing Sheets

US 8,999,723 B2

TRANSFORMER HYDROGEN INDICATOR

FIELD OF THE INVENTION

The present invention relates to apparatus and methods for detecting the presence of hydrogen in electrical transformers, and more particularly, a module assembly that may be attached to existing or new transformers and which includes a chemochromic indicator that changes color in the presence of hydrogen.

BACKGROUND OF THE INVENTION

The electric power industry has for many years recognized that thermal decomposition of the oil and other insulating materials within oil-insulated electrical apparatus can lead to the generation of a number of "fault gases." These phenomena occur in equipment such as oil filled transformers (both conservator and gas-blanketed types), load tap changers, transformer windings, bushings and the like. The detection of specific fault gases in electrical apparatus can be an important part of a preventative maintenance program.

The presence of fault gases in oil-blanketed transformers with conservators and other utility assets has well documented implications relating to the performance and operating safety of the transformer. There is a substantial body of knowledge available correlating the presence of gases with certain, identified transformer conditions and faults. It is therefore beneficial to monitor the condition of dielectric fluids in electric equipment as a means to maximize performance, and at the same time minimize wear and tear on the equipment, and to thereby minimize maintenance costs and down time. Thus, information relating to the presence or absence of certain fault gases in transformer oil can lead to greatly increased efficiency in the operation of the transformer.

The presence of certain fault gases in transformer oil can be indicative of transformer malfunctions, such as arcing, partial or coronal discharge. These conditions can cause mineral transformer oils to decompose generating relatively large quantities of hydrogen gas, which is highly volatile, and which in some instances may accumulate in a transformer under relatively high pressure. Left undetected or uncorrected, equipment faults can lead to an increased rate of degradation, and even to catastrophic explosion of the transformer. Transformer failure is a significantly expensive event for an electric utility, not only in terms of down time and the costs of replacement equipment, but also in terms of the costs associated with lost power transmission. From a safety perspective, it is imperative that line personnel and maintenance crews know if a particular operating transformer contains dangerous levels of hydrogen gas before approaching the unit. A visual indicator that indicates when hydrogen gas is present and which can be viewed from a safe distance, aided if necessary with a spotting scope, would provide a warning so that the transformer can be de-energized and removed for maintenance.

Despite the known need for reliable equipment to monitor gas in oil, designing equipment that holds up to the rigors of on-site conditions has been problematic for a variety of reasons. That said, there are a number of solutions known in the art. For example, mechanical/vacuum and membrane extraction methods and apparatus for degassing transformer oil are well known, as exemplified by U.S. Pat. No. 5,659,126. This patent discloses a method of sampling headspace gas in an electrical transformer, analyzing such gases according to a temperature and pressure dependent gas partition function, and based on the derived analysis predicting specific transformer faults.

An example of a gas extraction apparatus that relies upon a membrane tube for extraction of gas from transformer oil is disclosed in U.S. Pat. No. 4,112,737. This patent depicts a plurality of hollow membrane fibers, which are inserted directly into transformer oil in the transformer housing. The material used for the membrane is impermeable to oil, but gases dissolved in the oil permeate through the membrane into the hollow interior of the fibers. A portable analytical device such as a gas chromatograph is temporarily connected to the probe so that the test sample is swept from the extraction probe into the analytical device for analysis.

Although these devices have provided benefits, they have significant limitations when used to monitor smaller transformers used in connection with, for example, pole-mounted distribution transformers used by electric utilities. Not only are these types of transformers too difficult to access for routine monitoring, but the costs and difficulties associated with either extracting gas from or installing extractors into such small devices makes the foregoing types of monitoring unpractical.

Moreover, there are numerous practical problems remaining to the development of reliable apparatus for extraction, monitoring and analysis of fault gases in transformer oils. Many of these problems relate to the design of reliable fluid routing systems that are redundant enough to provide a relatively maintenance free unit. Since transformers are often located in exceedingly harsh environmental conditions, fluid routing problems are magnified. This is especially true given that the instruments needed to reliably analyze the gases are complex analytical instruments. Two patents that describe the difficulties of these engineering challenges are U.S. Pat. Nos. 6,391,096 and 6,365,105, both of which are incorporated herein by this reference. These two patents illustrate not only the complexities of the fluid routing systems needed, but solutions that have proved very reliable.

In addition to the examples given above, there are numerous other devices available for monitoring electrical asset oil for the presence of hydrogen and other gases. However, such devices tend to be very expensive and are therefore limited to larger electrical assets—the costs of the equipment and the monitoring programs that go with them are too high to justify using the devices with relatively smaller assets such as transformers used by utilities for routine power delivery systems. But the problems with fault gas accumulation in transformers are not limited to the large systems that can be monitored with existing systems such as those described above and the expenses that are caused by transformer failure are a significant part of many utilities' business. Accordingly, there is a need for a low cost device that allows utilities to monitor transformers to detect the presence of hydrogen.

SUMMARY OF THE INVENTION

The advantages of the present invention are achieved in a first preferred and illustrated embodiment of a hydrogen indicator for use with transformers. The indicator is defined by a module assembly that threads into either the headspace or into the oil-filled body of a transformer. The module has an open interior that contains a film that incorporates a hydrogen-sensitive chemochromic indicator. The indicator film is visible through a lens. When the film has been exposed to hydrogen, chemical changes in the chemochromic indicator cause the film to change color—the color change is immediately visible through the lens. Accordingly, a utility worker is able to determine when hydrogen has been generated in the transformer with a quick visual inspection of the module.

The hydrogen indicator of the present invention provides a reliable, low cost device for determining when dangerous levels of hydrogen gas have been generated in a transformer.

BRIEF DESCRIPTION OF THE DRAWINGS

The invention will be better understood and its numerous objects and advantages will be apparent by reference to the following detailed description of the invention when taken in conjunction with the following drawings.

In FIG. 2 the module is shown as being schematically installed in a transformer.

DETAILED DESCRIPTION OF PREFERRED AND ILLUSTRATED EMBODIMENTS

Figure 1:
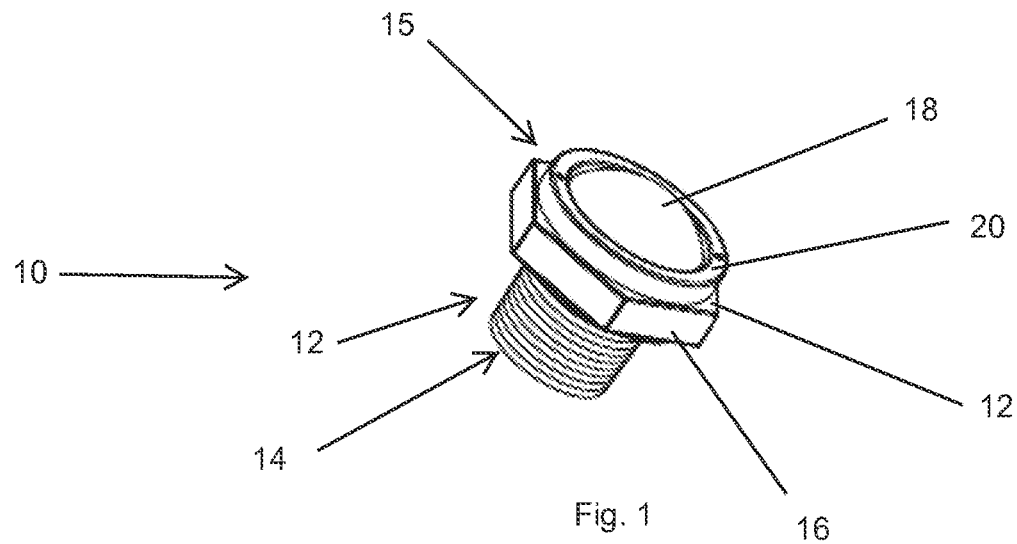
FIG. 1 is a perspective view of a first illustrated embodiment of the module of the present invention shown in an assembled condition.
Figure 2:
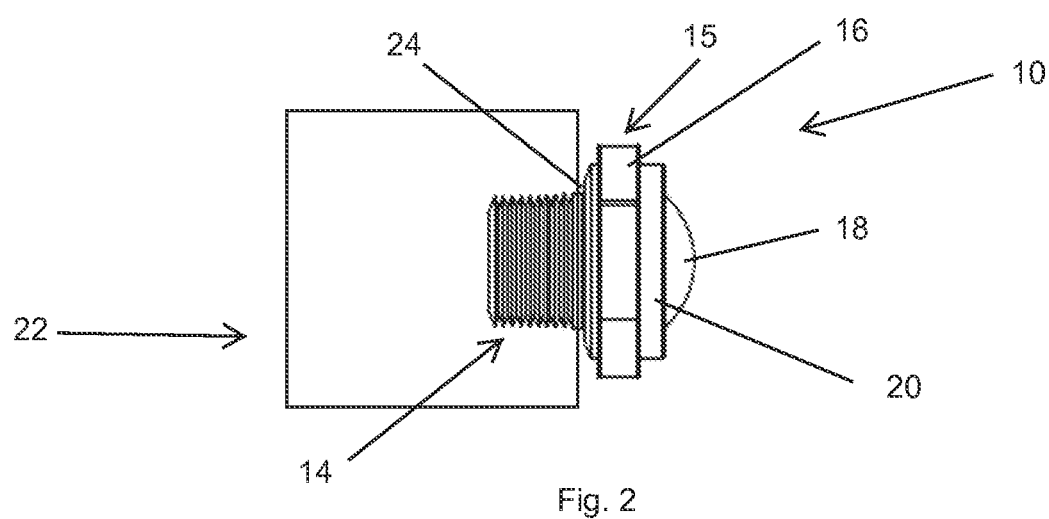
FIG. 2 is side elevation view of the module shown in FIG. 1.
Figure 3:
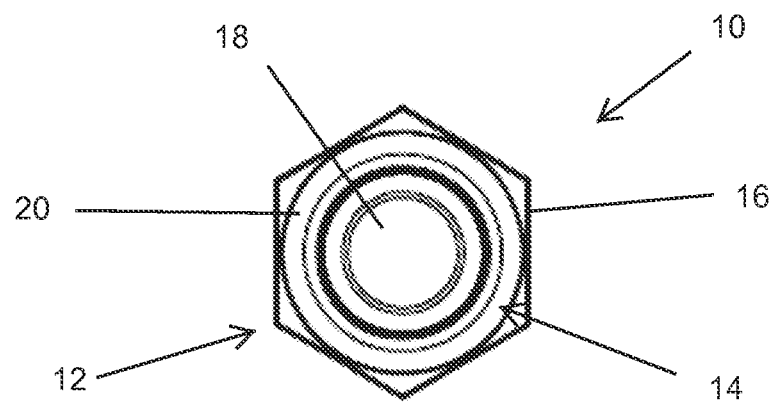
FIG. 3 is an end view of the module shown in FIG. 1, with the view looking toward the module's threaded and installed end.

With reference to FIGS. 1 through 3, a transformer hydrogen indicator module 10 according to the present invention is shown in an assembled state. The module 10 comprises a body 12 having a threaded end 14 that is in use threaded into a threaded opening in a transformer, and an exposed end 15 that preferably is defined in part by a hexagonal head 16 and which in use is located externally of the transformer. A translucent lens 18 is found on the exposed end and is held in place in the assembled module with a collar clamp ring 20.

A transformer 22 is shown schematically in FIG. 2 with module 10 threaded into a threaded port 24 in the transformer—the port 24 opens to the interior of the transformer where the insulating oil is contained. The port 24 may be positioned either above or below the level of insulating oil contained in the transformer. That is, the module 10 may be located in the transformer such that the module is in the headspace above the oil, or such that the module's interior end is immersed in the oil. In either case, the module 10 is threaded into the threaded port 24 and snugly tightened to prevent leaks—gaskets may be used as necessary to insure a leak-free seal between the module 10 and the transformer 22.

Figure 4:
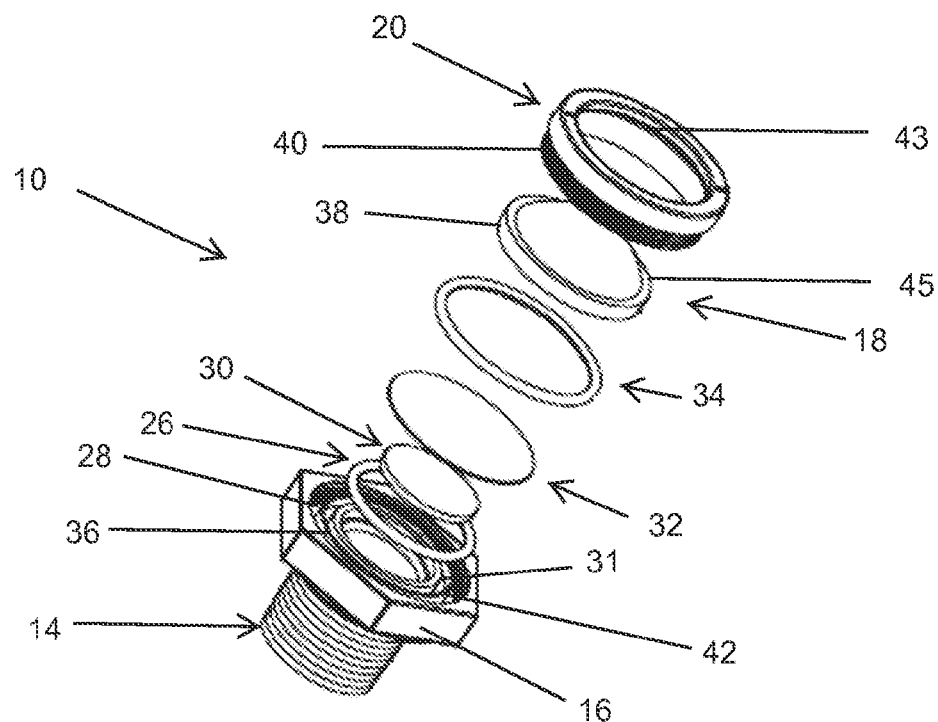
FIG. 4 is a perspective and exploded view of a first illustrated embodiment of the module of the present invention, illustrating the component parts of the assembly.

Turning to FIG. 4, a first illustrated embodiment of module 10 is illustrated in an exploded view to show the component parts. The exposed end 15 of body 12 is configured to receive the various components described below and to insure a leak-free environment so that oil and/or gas contained within transformer 22 into which module 10 is installed cannot escape through the module.

A first O-ring 26 is received in a circumferential inner O-ring seat 28 formed in body 12 and a frit 30 is positioned within the circumference of first O-ring 26 such that the frit rests on an annular seat 31 on the body 12 inwardly of inner seat 28. Frit 30 is preferably a porous disk material through which oil and/or other liquids and gas readily flow. Frit 30 is preferably sintered bronze but may be fabricated from other porous materials including sintered glass, sintered metals, or wire mesh and other materials.

Immediately adjacent frit 30 is an indicator film 32. Indicator film 32 is a film that is treated with a chemochromic indicator material that is sensitive to hydrogen so that when the film is exposed to hydrogen the color of the film changes. It will be appreciated that the indicator film 32 is of the type described in U.S. Pat. No. 6,895,805, the disclosure of which is incorporated herein by this reference. The indicator film 32 may be either of the type that reversibly changes color on exposure to hydrogen, or of the type that irreversibly changes color, or a combination of both types. In the assembled module 10, frit 30 lies adjacent to indicator film 32 and the frit provides support for the film to prevent mechanical damage to it.

The indicator film 32 is preferably defined by a multi-layered sheet having at least a gas sensor layer and an adjacent carrier layer onto which the gas sensor layer is deposited. The carrier layer makes handling of the indicator film easier and may be any appropriate sheet material cut into desired shapes and sizes.

A second O-ring 34 has a diameter sized so that the 0-ring is received in an outer circumferential O-ring seat 36 formed in body 12—O-ring 34 and seat 36 are larger in diameter than first O-ring 26 and inner O-ring seat 28; all of these components are arranged such that they share a common axis through body 12. Lens 18 is a translucent material such as glass or appropriate plastics and has a base 38 that defines a diameter that is the same size as second O-ring 34. In the assembled module 10, the base 38 of lens 18 lies on O-ring 34.

The components described above and shown in FIG. 4 are held sandwiched together with collar clamp ring 20, which has a threaded base 40 that threads into a threaded seat 42 in body 12. As the collar clamp ring 20 is threaded onto body 12, the clamp ring compresses all of the components shown in FIG. 4 to define a leak-free assembly. More specifically, an inwardly projecting annular ledge 43 bears against an upper annular edge 45 of lens 18 and as the clamp ring 29 is tightened, it compresses the various components together in body 12 to form a leak-free seal.

Figure 5:
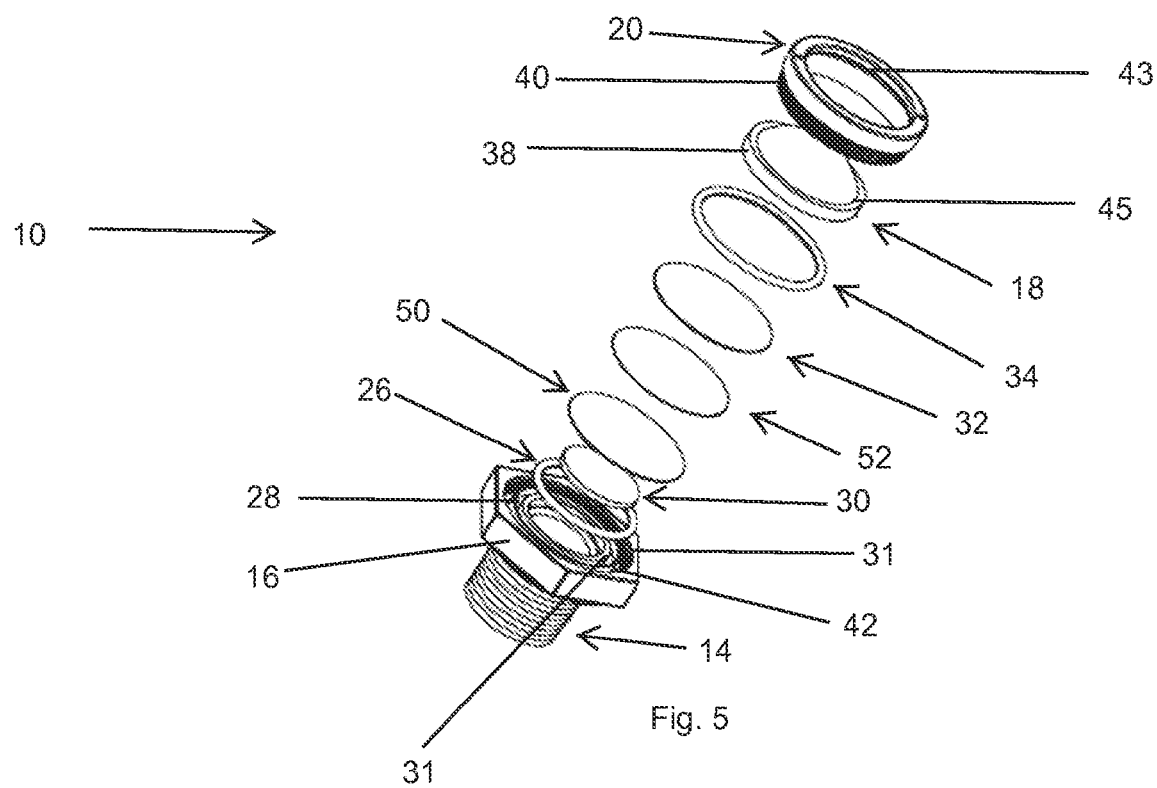
FIG. 5 is a perspective and exploded view of a second illustrated embodiment of the module of the present invention, illustrating the component parts of the assembly.

The second illustrated embodiment of a module 10 shown in exploded view in FIG. 5 is identical to the embodiment of FIG. 4 except that in FIG. 5 the assembly includes (a) a gas permeable membrane 50 immediately adjacent to and externally of frit 30 and interiorly of indicator film 32, and (b) a porous spacer 52 adjacent to and externally of the gas permeable membrane 50. As may be seen in FIG. 5, the membrane 50 and spacer 52 thus are interposed between and separate the indicator film 32 from the frit 30. Gas permeable membrane 50 is preferably fabricated from fluorosilcone or polytetrafluoroethyne (i.e., PTFE or TEFLON) because those materials are very stable in a hydrocarbon environment such as electrical insulating oils and have excellent gas transmission properties for the gas species of interest here—hydrogen. The porous spacer 52 is preferably a paper material that is not degraded by hydrogen or other gases that are present in the insulating oil in the system described herein; filter-type papers have been found to work well in this environment but there are numerous other materials such as cotton and other fibrous pads that will work. The porous spacer 52 physically separates the adjacent membrane 50 from the indicator film 32 and thereby defines a space through which gas and/or oil may flow and thereby expose the indicator film 32.

The interior of body 12 is open so that the indicator film 32 is exposed to either or both the gas and/or oil contained in the transformer 22, depending on the location of the module 10 in the transformer 22.

The hydrogen indicator module 10 may be installed into a transformer either during its manufacture or by retrofitting after installation. In either case, the module is threaded into a threaded port in the transformer as indicated above, with the interior of the module either in the headspace above the insulating oil or immersed in the oil. Preferably, the module is oriented so that an inspector may view the lens 18 from the ground or another convenient location, either unassisted or with a spotting scope. If the indicator film has been exposed to hydrogen (either gas dissolved in oil or free gas in the headspace), the indicator film exhibits a change in color compared to a control indicator, which has not been exposed to hydrogen.

In view of the many possible embodiments to which the principles of our invention may be applied, it should be recognized that the detailed embodiments are illustrative only and should not be taken as limiting the scope of the invention. Rather, I claim as my invention all such embodiments as may come within the scope and spirit of the following claims and equivalents thereto.

The invention claimed is:

1. A transformer hydrogen gas indicator, comprising:
    a module having a first end adapted for insertion into a transformer and a second end exposed externally of the transformer, the module having a body with an open interior;
    a chemochromic indicator in the open interior of the body; and
    a translucent lens on the second end of the module.

2. The transformer hydrogen gas indicator according to claim 1 wherein the chemochromic indicator is sensitive to hydrogen gas and changes color when exposed to hydrogen gas.

3. The transformer hydrogen gas indicator according to claim 2 including a frit adjacent the chemochromic indicator, said frit comprising a material porous to oil and hydrogen gas and said frit supporting said chemochromic indicator.

4. The transformer hydrogen gas indicator according to claim 3 wherein the frit is a sintered bronze material.

5. The transformer hydrogen gas indicator according to claim 4 including a gas permeable membrane between said frit and said chemochromic indicator.

6. The transformer hydrogen gas indicator according to claim 5 including a porous spacer between the permeable membrane and said chemochromic indicator.

7. The transformer hydrogen gas indicator according to claim 6 wherein said gas permeable membrane is defined by a fluorosilicone material.

8. The transformer hydrogen gas indicator according to claim 6 wherein said porous spacer is a paper material.

9. The transformer hydrogen gas indicator according to claim 2 in which the chemochromic indicator reversibly changes color upon exposure to hydrogen gas.

10. The transformer hydrogen gas indicator according to claim 2 in which the chemochromic indicator irreversibly changes color upon exposure to hydrogen gas.

11. The transformer hydrogen gas indicator according to claim 2 in which a portion of the chemochromic indicator reversibly changes color upon exposure to hydrogen gas and a portion of the chemochromic indicator irreversibly changes color upon exposure to hydrogen gas.

12. A transformer hydrogen gas indicator, comprising:
    a body having a threaded first end, a second end with a translucent lens and an open interior between the first and second ends; and
    a film retained in the body, said film comprising a chemochromic indicator compound adapted for changing color in the presence of hydrogen gas.

13. The transformer hydrogen gas indicator according to claim 12 in which the chemochromic indicator reversibly changes color upon exposure to hydrogen gas.

14. The transformer hydrogen gas indicator according to claim 12 in which the chemochromic indicator irreversibly changes color upon exposure to hydrogen gas.

15. The transformer hydrogen gas indicator according to claim 12 in which a portion of the chemochromic indicator reversibly changes color upon exposure to hydrogen gas and a portion of the chemochromic indicator irreversibly changes color upon exposure to hydrogen gas.

16. A method of monitoring a transformer for the presence of hydrogen gas, comprising the steps of:
    a) providing a transformer with insulating oil;
    b) inserting an indicator module into the transformer, the indicator module having a chemochromic indicator retained therein and exposed to an interior space of said transformer containing insulating oil, said indicator module inserted into the transformer such that the chemochromic indictor is visually apparent externally of the transformer;
    c) visually inspecting the indicator module to determine if the chemochromic indicator has changed from a first color to a second color; and
    d) based on the determination of color change in step c) determining if hydrogen gas is present in the transformer.

17. The method according to claim 16 further comprising the steps of inserting said indicator module into the transformer so that said chemochromic indicator is directly exposed to said insulating oil.

18. The method according to claim 16 further comprising the steps of inserting said indicator module into the transformer so that said chemochromic indicator is exposed to a headspace in said transformer above said insulating oil.

19. The method according to claim 18 wherein said chemochromic indicator is not directly exposed to said insulating oil.

* * * * *